US009615825B2

(12) United States Patent
Viola

(10) Patent No.: US 9,615,825 B2
(45) Date of Patent: Apr. 11, 2017

(54) RELEASE TOOL FOR AN END EFFECTOR OF A SURGICAL STAPLING APPARATUS

(71) Applicant: Covidien LP, Mansfield, MA (US)

(72) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 488 days.

(21) Appl. No.: 14/143,520

(22) Filed: Dec. 30, 2013

(65) Prior Publication Data

US 2014/0203062 A1 Jul. 24, 2014

Related U.S. Application Data

(60) Provisional application No. 61/754,170, filed on Jan. 18, 2013.

(51) Int. Cl.
| | | |
|---|---|---|
| A61B 17/064 | (2006.01) | |
| A61B 17/072 | (2006.01) | |
| A61B 90/00 | (2016.01) | |
| A61B 17/00 | (2006.01) | |
| A61B 90/70 | (2016.01) | |

(52) U.S. Cl.
CPC ...... *A61B 17/064* (2013.01); *A61B 17/07207* (2013.01); *A61B 90/08* (2016.02); *A61B 90/70* (2016.02); *A61B 2017/00398* (2013.01); *A61B 2017/00473* (2013.01); *A61B 2017/00477* (2013.01); *A61B 2017/07278* (2013.01)

(58) Field of Classification Search
CPC .. A61B 2017/07214; A61B 2017/0728; A61B 17/115; A61B 17/128; A61B 17/076; A61B 17/068
USPC .................. 227/175.1, 87, 111; 606/75, 219
See application file for complete search history.

(56) References Cited

U.S. PATENT DOCUMENTS

| | | | | |
|---|---|---|---|---|
| 6,021,854 A | * | 2/2000 | Scarola ................... | B25F 5/021 173/141 |
| 7,568,605 B2 | * | 8/2009 | Kruszynski .......... | A61B 17/072 227/175.1 |
| 2009/0206130 A1 | * | 8/2009 | Hall ................. | A61B 17/07207 227/175.2 |
| 2009/0314821 A1 | | 12/2009 | Racenet | |

(Continued)

FOREIGN PATENT DOCUMENTS

| | | |
|---|---|---|
| EP | 2499987 A2 | 9/2012 |
| WO | 2009039506 A1 | 3/2009 |
| WO | 2011/087462 A1 | 7/2011 |

OTHER PUBLICATIONS

Extended European Search Report issued in corresponding EP Appln. No. 14151671.6 dated Nov. 3, 2016.

*Primary Examiner* — Thanh Truong
*Assistant Examiner* — Dariush Seif

(57) ABSTRACT

A release tool is provided for an end effector with a pair of jaw members and a drive beam assembly configured for axial movement through the pair of jaw members. The release tool includes an elongate body member, a gripping assembly, and a release bar. The gripping assembly is secured to the elongate body member and is configured to secure the elongate body member to the end effector. The release bar is supported by the elongate body member and is axially movable relative to elongate body member. The release bar is configured to engage a beam of the drive beam assembly to retract the beam to a proximal position when the beam is disposed in a position distal of the proximal position.

20 Claims, 13 Drawing Sheets

(56) References Cited

U.S. PATENT DOCUMENTS

| | | | |
|---|---|---|---|
| 2010/0089970 A1* | 4/2010 | Smith | A61B 17/07207 227/175.1 |
| 2011/0121049 A1 | 5/2011 | Malinouskas et al. | |
| 2011/0163147 A1 | 7/2011 | Laurent et al. | |
| 2013/0214024 A1* | 8/2013 | Takei | A61B 17/068 227/175.1 |

* cited by examiner

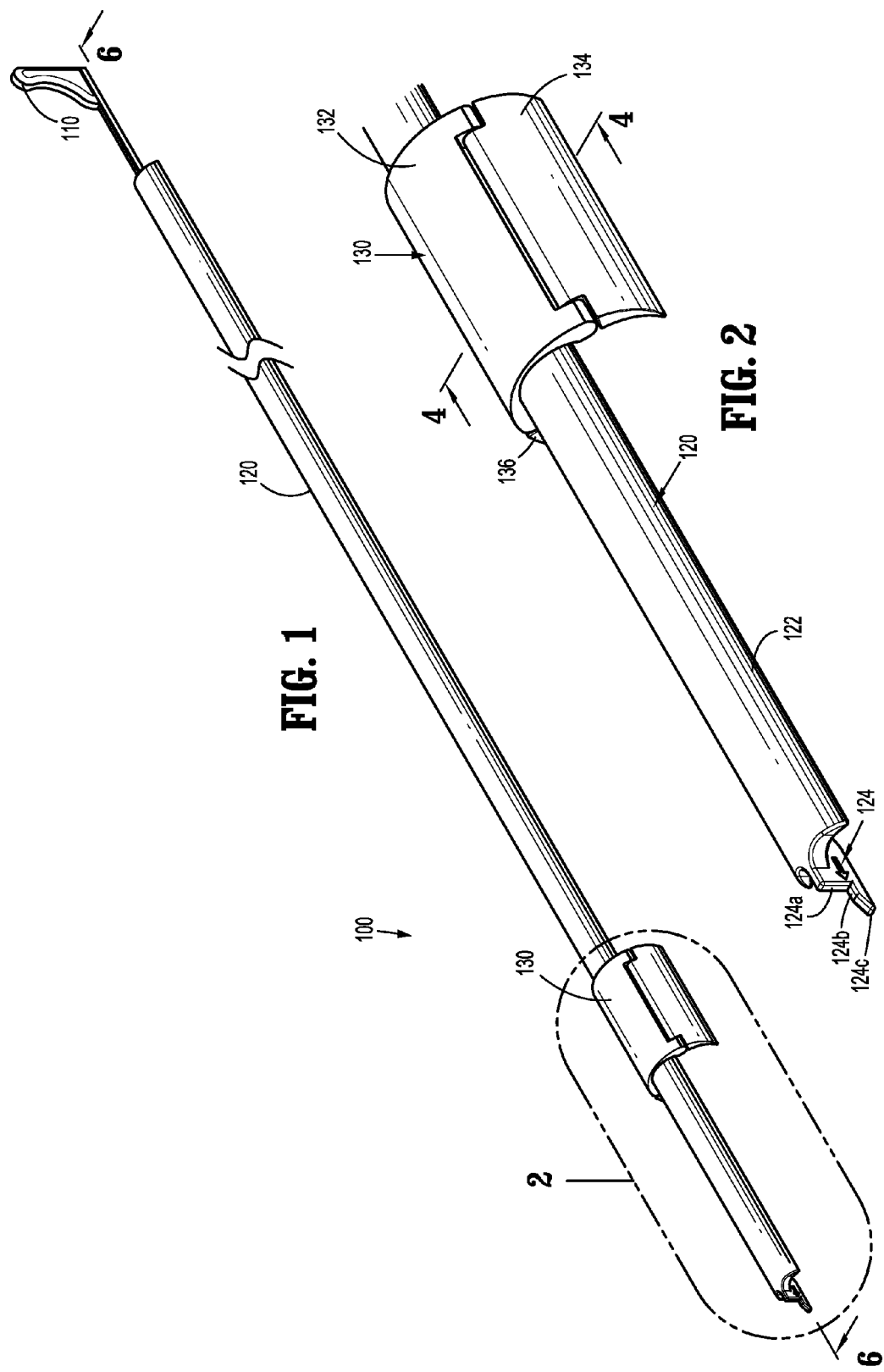

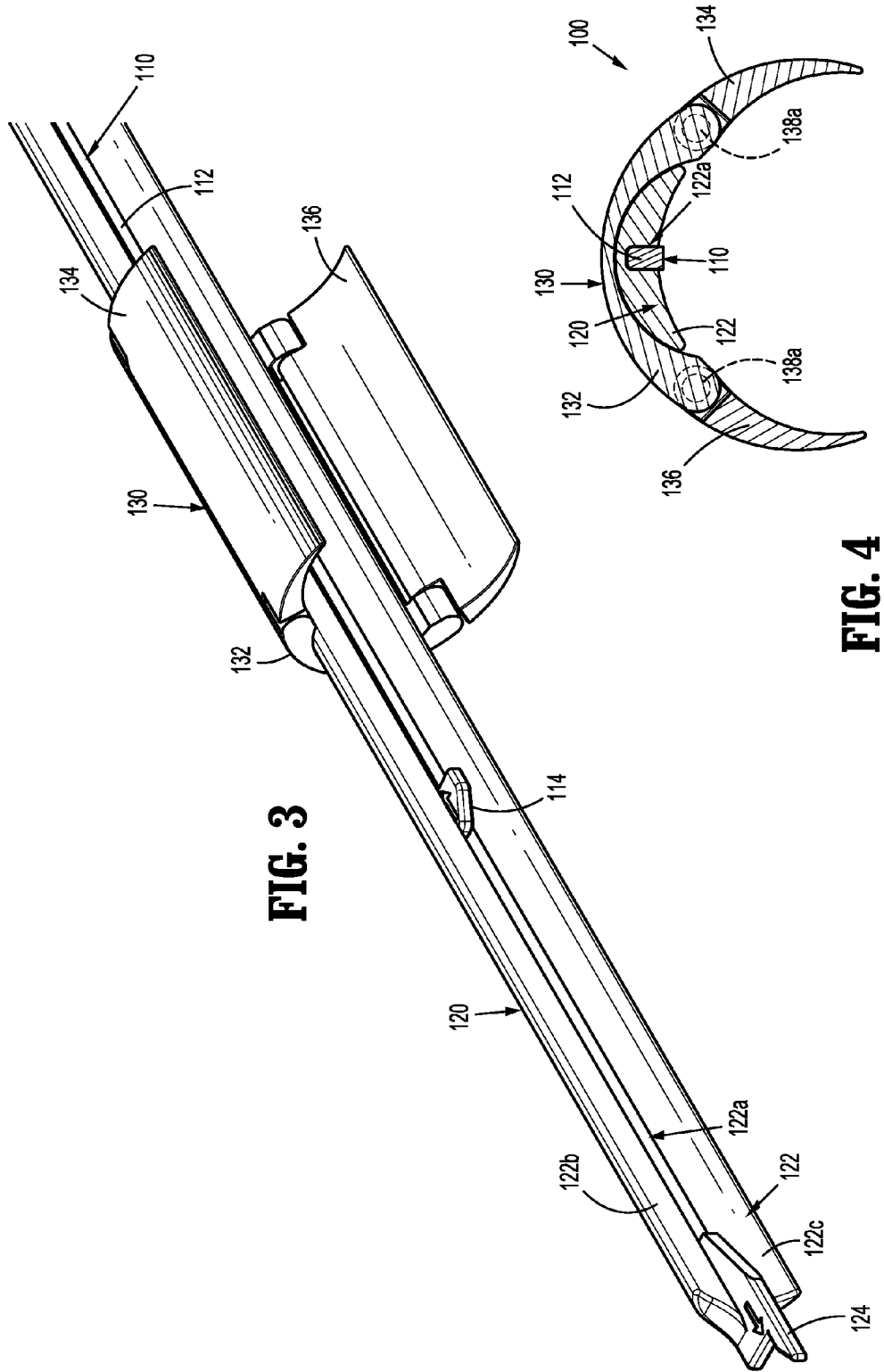

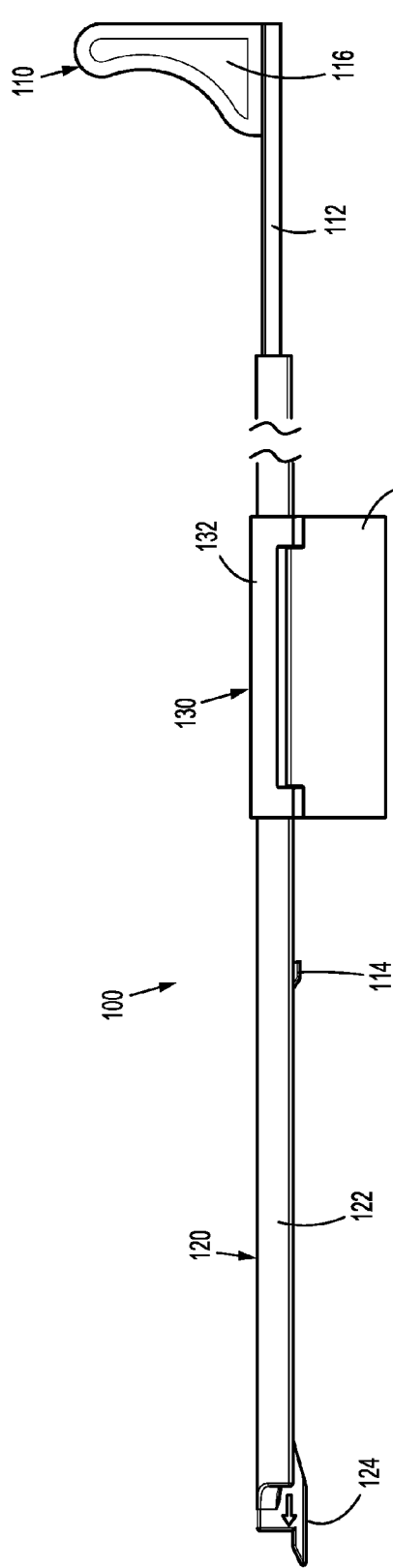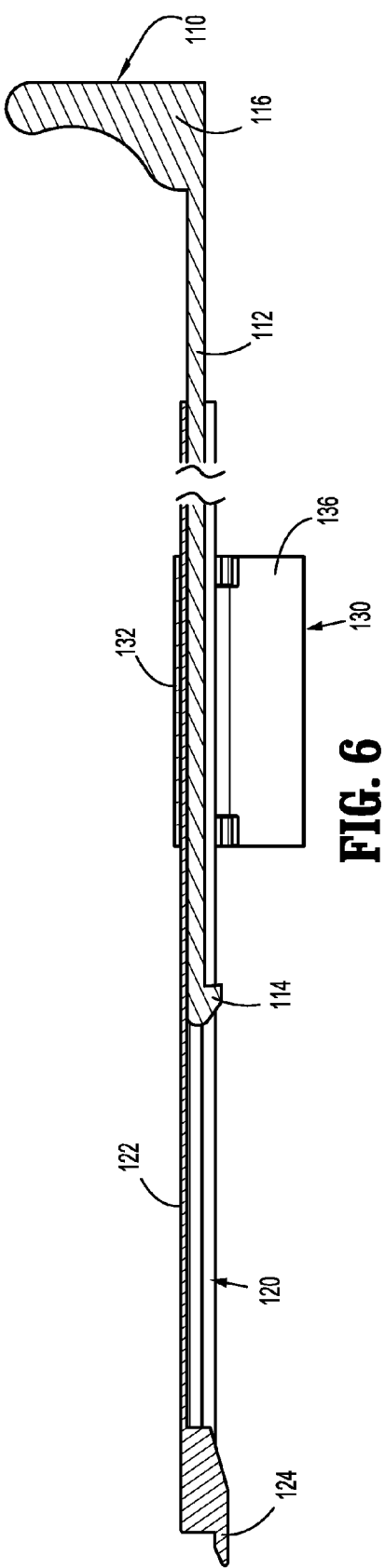

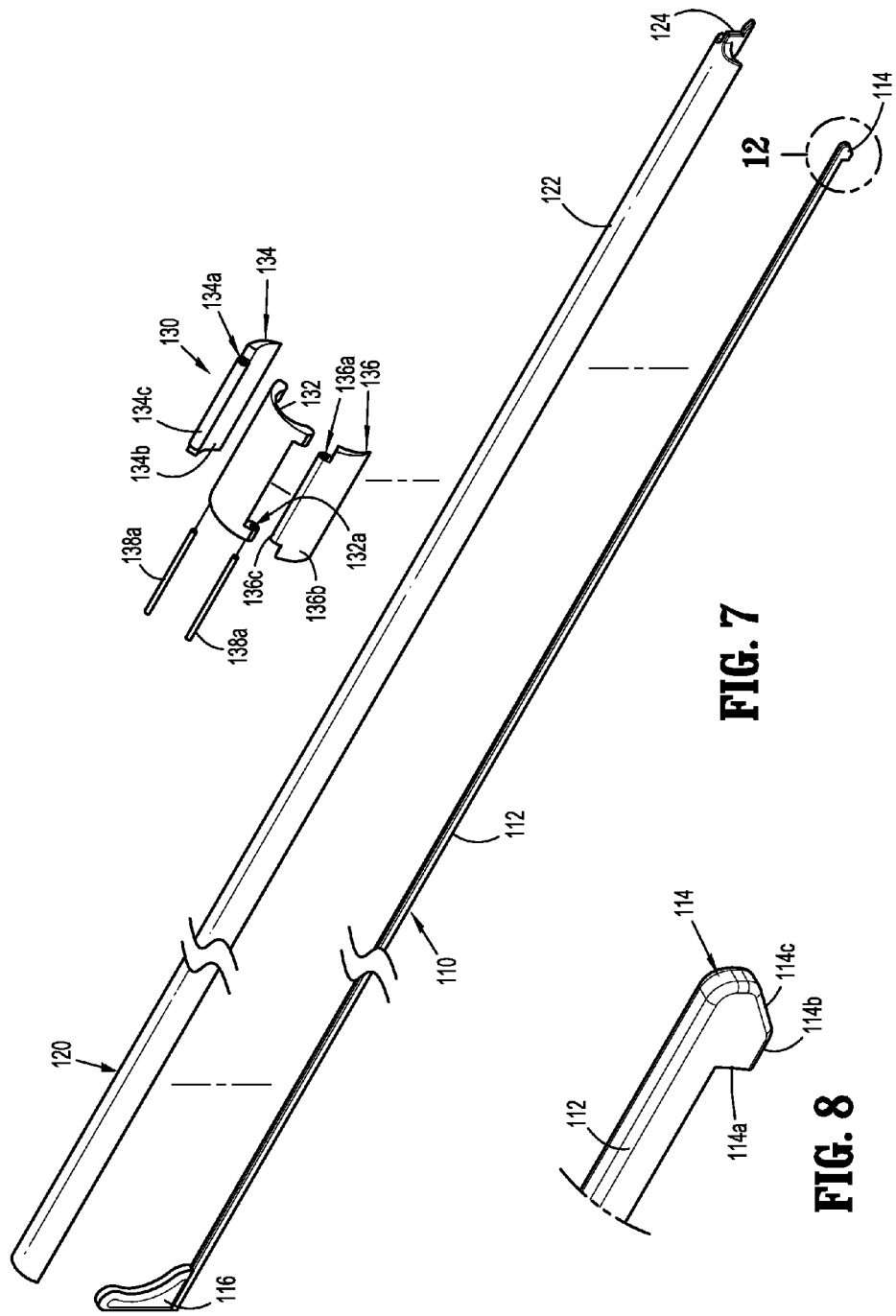

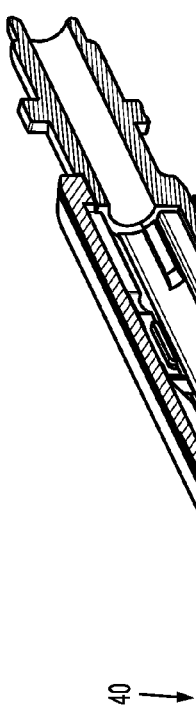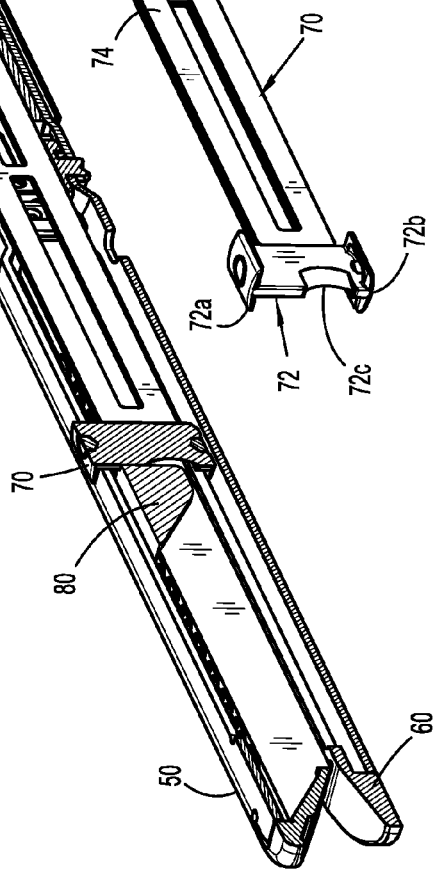
FIG. 10
FIG. 11

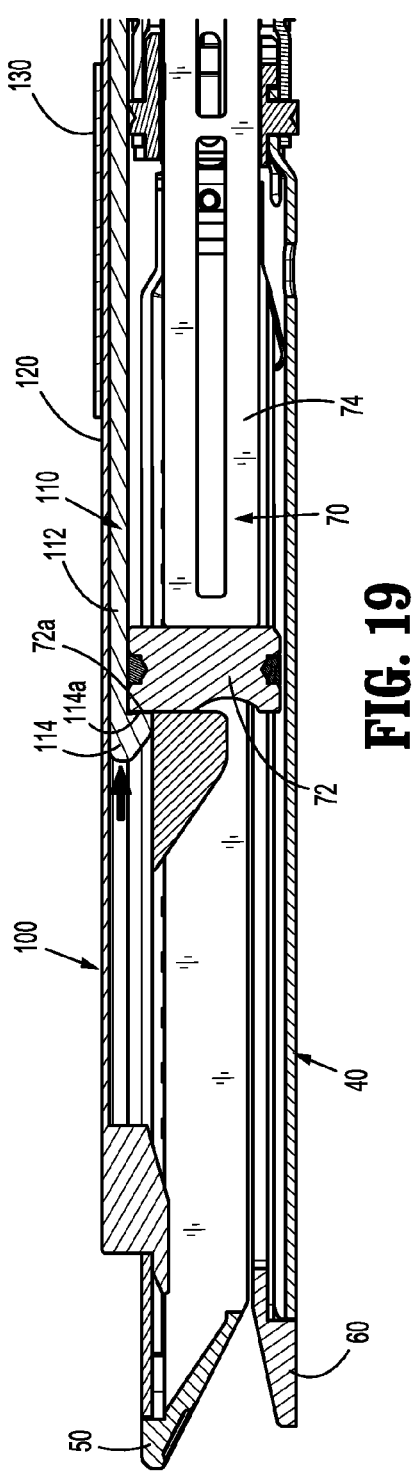
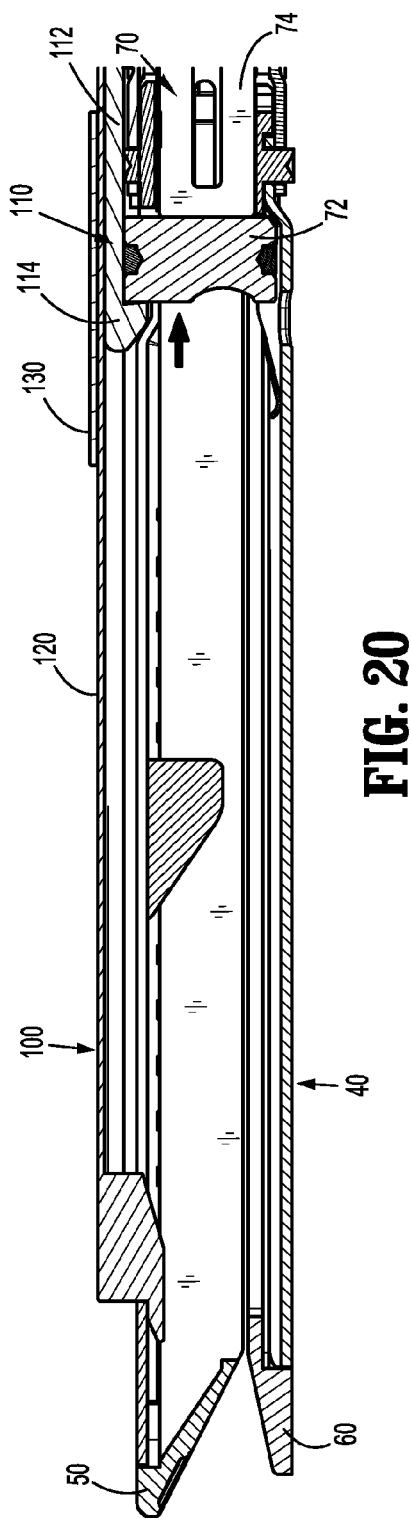
FIG. 19
FIG. 20

RELEASE TOOL FOR AN END EFFECTOR OF A SURGICAL STAPLING APPARATUS

CROSS-REFERENCE TO RELATED APPLICATIONS

The present application claims priority to, and the benefit of, U.S. Provisional Patent Application Ser. No. 61/754,170, filed on Jan. 18, 2013, the entire contents of which are hereby incorporated by reference.

BACKGROUND

1. Technical Field

The present disclosure relates to surgical devices and/or systems and their methods of use. More specifically, the present disclosure relates to release tools and assemblies configured for use with electromechanical, hand-held surgical apparatuses, devices and/or systems with end effectors for clamping, cutting and/or stapling tissue.

2. Background of Related Art

Some electromechanical surgical devices, surgical staplers for example, may include end effectors with a pair of jaw members that support a plurality of fasteners. These jaw members cooperate to clamp, cut, and/or staple tissue disposed between the jaw members. On occasion, tissue may become undesirably entrapped between the jaw members during operation of these surgical staplers. In order to dislodge the entrapped tissue, typically the stapling devices are operated in reverse. However, in some instances, in order to dislodge the entrapped tissue, the tissue and the surgical stapling apparatus are often required to be manipulated in a manner requiring additional surgical steps on the entrapped and/or surrounding tissue. As such, it would be desirable to have a surgical device that can easily and effectively release tissue that is undesirably entrapped between the jaw members while limiting unnecessary tissue damage.

SUMMARY

According to one aspect, the present disclosure relates to a release tool for an end effector with a pair of jaw members and a drive beam assembly configured for axial movement through the pair of jaw members. The release tool includes an elongate body member, a gripping assembly, and a release bar.

The elongate body member has distal and proximal ends. The distal end of the elongate body member includes a distal hook member.

The gripping assembly is secured to the elongate body member and is configured to secure the elongate body member to the end effector. The gripping assembly includes a panel that pivots relative to the elongate body member. In embodiments, the gripping assembly includes a first panel and a second panel that pivot in opposing directions relative to the elongate body member.

The release bar is supported by the elongate body member and is axially movable relative to elongate body member. The release bar is configured to engage a beam of the drive beam assembly to retract the beam to a proximal position when the beam is disposed in a position distal of the proximal position. The release bar includes a beam engaging hook, a drive member, and a handle. The beam engaging hook is configured to engage the beam upon the proximal movement of the beam engaging hook so that the beam engaging hook retracts the beam to the proximal position. The drive member is secured to the beam engaging hook and is axially movable to axially move the beam engaging hook. The beam engaging hook is supported on a distal end of the drive member. The handle is supported on a proximal end of the drive member.

According to another aspect, the present disclosure relates to a release tool and end effector kit. The kit includes an end effector and a release tool. The end effector includes a pair of jaw members and a beam supported on a drive assembly configured for axial movement through the pair of jaw members. The release tool is selectively attachable to the end effector. The release tool includes an elongate body member, a gripping assembly, and a release bar including a beam engaging hook.

The gripping assembly is secured to the elongate body member to secure the elongate body member to the end effector. The distal end of the elongate body member includes a hook member. The gripping assembly includes a panel that pivots or otherwise rotates relative to the elongate body member.

The beam engaging hook of the release bar is supported by the elongate body member and is axially movable relative to the end effector when the elongate body member is secured to the end effector. The beam engaging hook is axially movable relative to the elongate body member. The beam engaging hook is engageable with the beam to retract the beam and drive beam assembly to a proximal position when the beam is disposed in a position distal of the proximal position. The pair of jaw members moves from a closed configuration to an open configuration when the beam engaging hook retracts the beam to the proximal position. The pair of jaw members includes an anvil member and a cartridge member. The cartridge member is configured to receive a cartridge that retains a plurality of fasteners.

According to yet another aspect, a surgical stapling kit includes a surgical stapling apparatus and a release tool.

The surgical stapling apparatus including an end effector, the end effector including an anvil supporting member, a cartridge receiving member, and a beam supported on a drive beam assembly that moves axially through the anvil supporting member and the cartridge receiving member. The release tool is selectively attachable to the end effector and includes an elongate body member, a pair of panels, and a release bar including a beam engaging member.

The pair of panels are secured to the elongate body member to secure the release tool to the end effector. The panels pivot relative to the elongate body member to secure the release tool to the end effector.

The release bar is supported by the elongate body member and is axially movable relative to the end effector when the release tool is secured to the end effector. The beam engaging member of the release bar is axially movable relative to the elongate body member. The beam engaging member is engageable with the beam to retract the beam and the drive beam assembly to a proximal position when the beam is disposed in a position distal of the proximal position. The anvil supporting member and the cartridge receiving member of the end effector move from a closed configuration to an open configuration when the beam engaging member of the release tool retracts the beam and the drive beam assembly to the proximal position.

The cartridge receiving member of the end effector defines a channel through a top surface thereof. A top portion of the beam axially translates through the channel upon the axial movement of the beam. The elongate body member of the release tool includes a distal hook member that is positionable within the channel. A proximal surface of the beam engaging member of the release bar contacts a distal surface of the top portion of the beam when the beam engaging member and the beam are engaged.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a perspective view of a release tool or assembly in accordance with the present disclosure;

FIGS. 2 and 3 are enlarged respective top and bottom perspective views of a distal end of the presently disclosed release tool or assembly;

FIG. 4 is an enlarged cross-sectional view of the presently disclosed release tool or assembly taken along line 4-4 of FIG. 2;

FIG. 5 is a side view of the presently disclosed release tool or assembly;

FIG. 6 is a longitudinal, cross-sectional view of the presently disclosed release tool or assembly taken along line 6-6 of FIG. 1;

FIG. 7 is a perspective view, with parts separated, of the presently disclosed release tool or assembly;

FIG. 8 is an enlarged view of the indicated area of detail of FIG. 7;

FIG. 10 is a longitudinal, cross-sectional view of the end effector shown in a partially fired condition;

FIG. 11 is a perspective view of a drive beam of the end effector;

FIGS. 19-20 are progressive cross-sectional views of the release tool or assembly retracting the drive beam of the end effector to a proximal position.

DETAILED DESCRIPTION OF EMBODIMENTS

Figure 9:
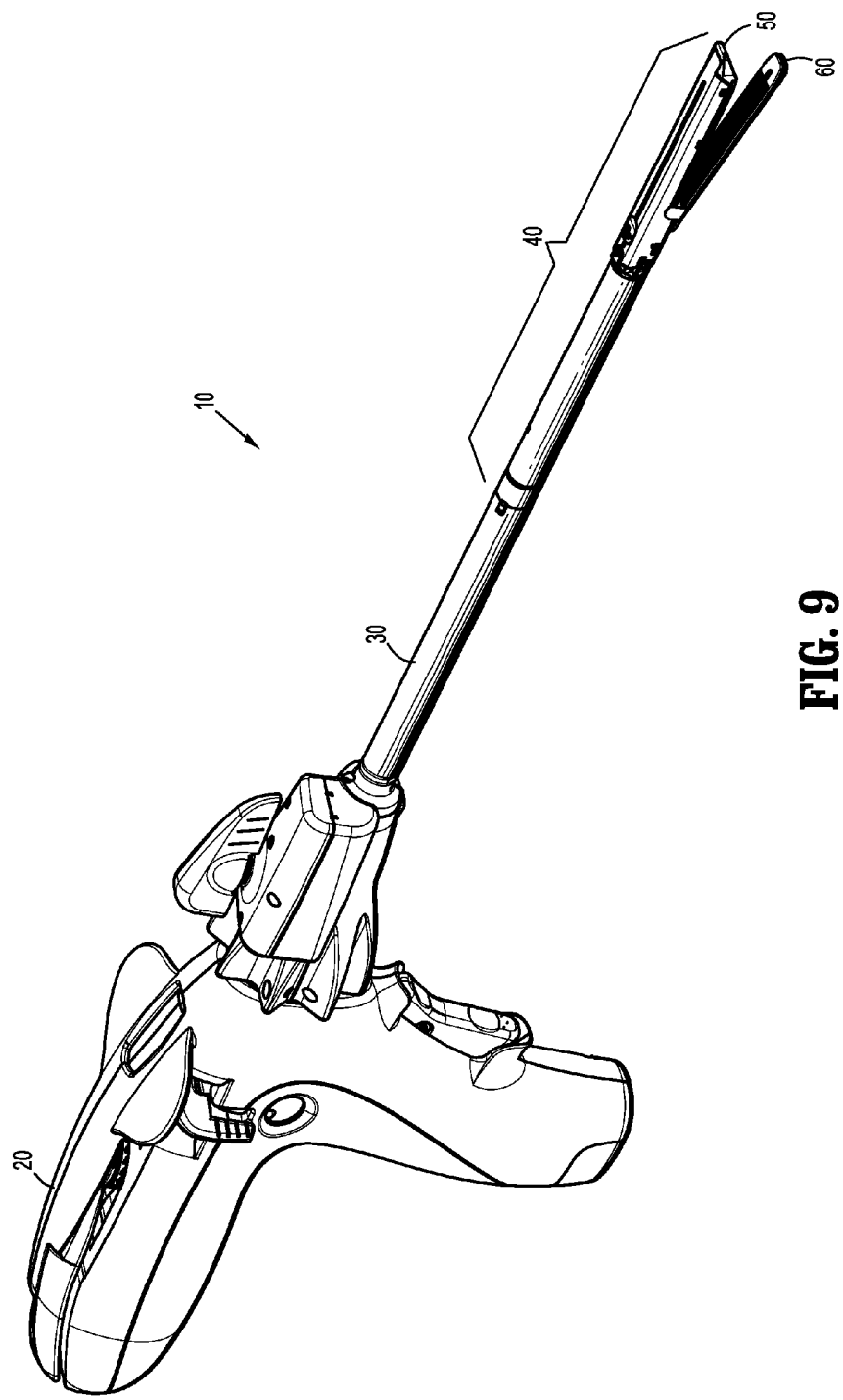
FIG. 9 is a perspective view of an exemplary surgical stapling apparatus.
Figure 12:
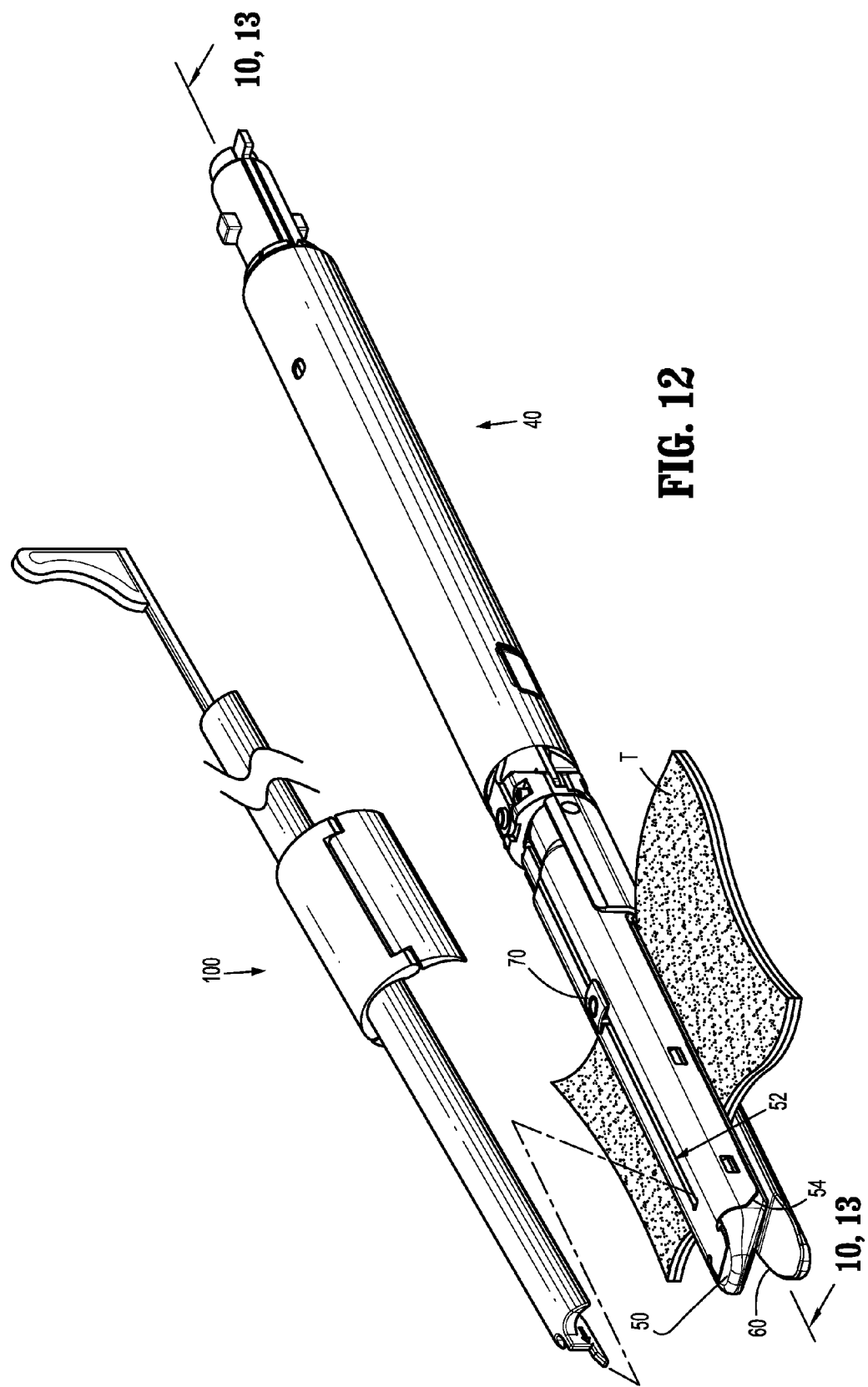
FIG. 12 is a perspective view of the presently disclosed release tool or assembly and an end effector of the surgical stapling apparatus, the end effector being shown in a partially fired condition while grasping tissue.
Figure 13:
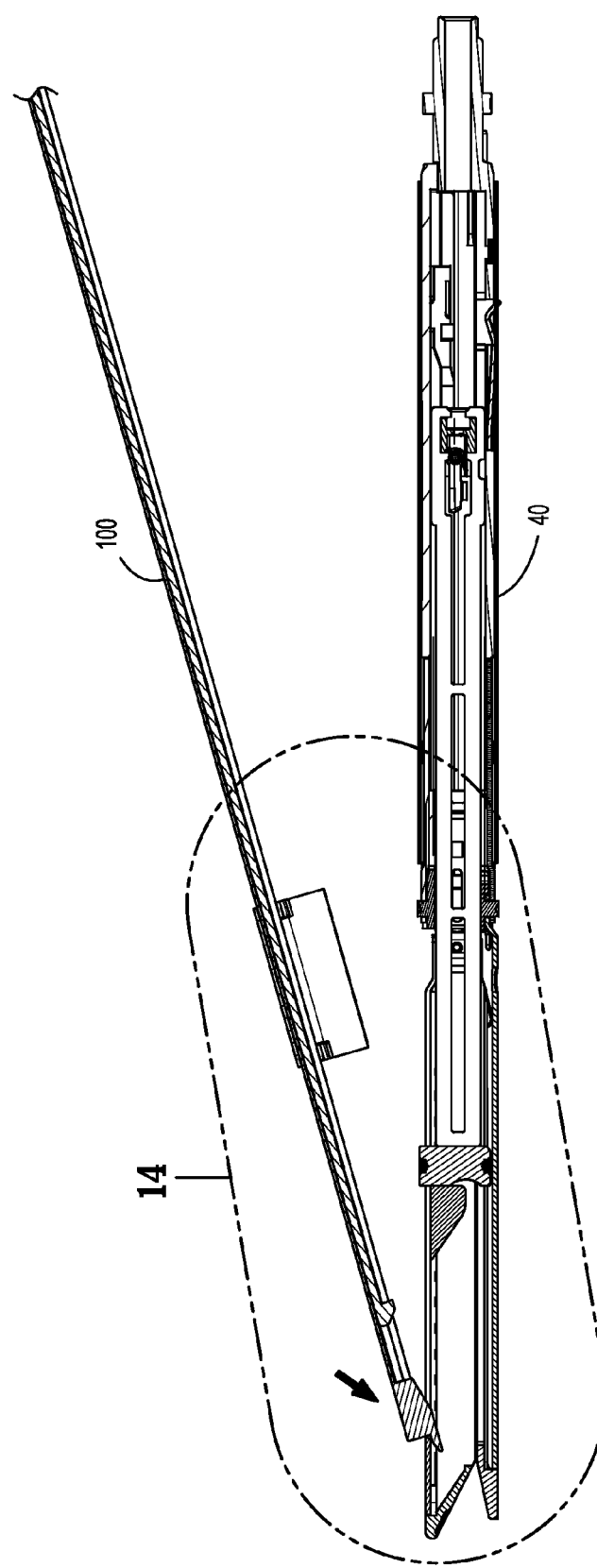
FIGS. 13-18 are progressive cross-sectional views of the presently disclosed release tool or assembly being mounted on the end effector.
Figure 14:
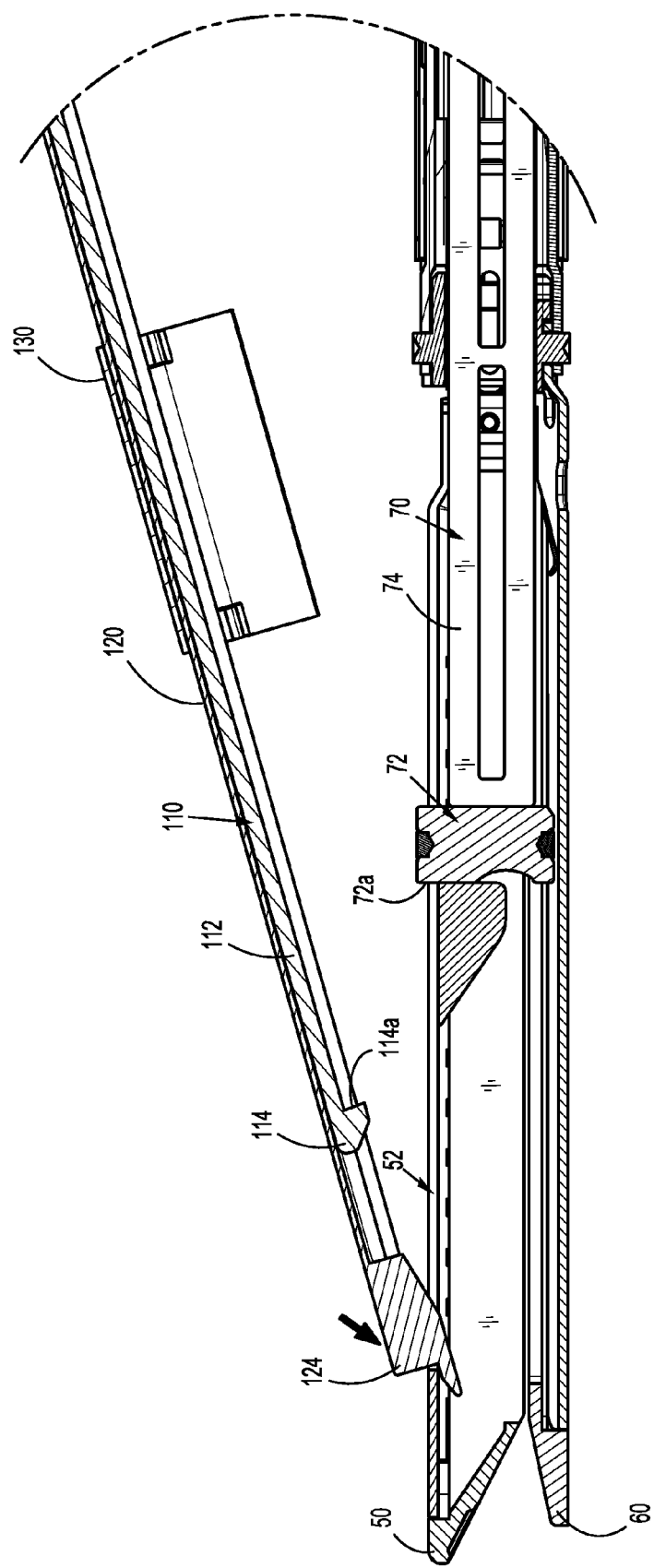
Figure 15:
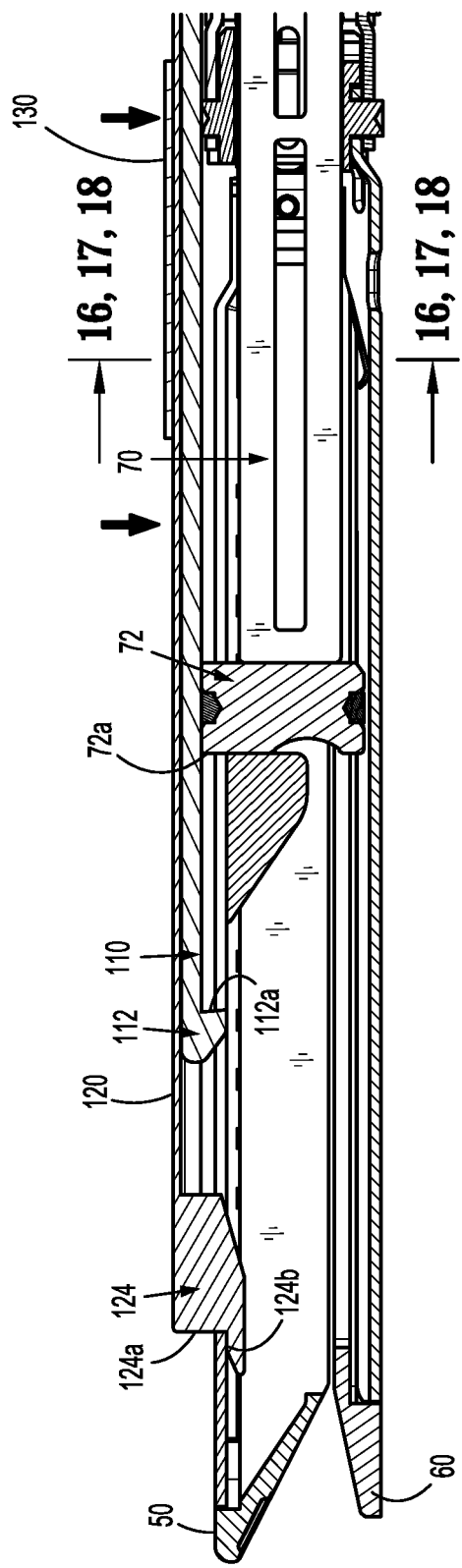

Embodiments of the presently disclosed surgical devices are described in detail with reference to the drawings, in which like reference numerals designate identical or corresponding elements in each of the several views. The term "clinician", as used herein, refers to a surgeon or surgical nurse. The term "distal" refers to that portion of the device, or component thereof, which is farthest from the clinician during proper use of the device, while the term "proximal" refers to that portion of the device, or component thereof, which is closest to the clinician during proper use of the device.

Referring initially to FIGS. 1-8, a release tool or assembly 100 includes a release bar 110, an elongate body member 120, and a gripping assembly 130.

Elongate body member 120 includes a body 122 that defines a longitudinal channel 122a which extends along a longitudinal axis defined by the body 122 between proximal and distal ends of the body 122. Body 122 includes a first half-section 122b, a second half-section 122c, and a distal hook member 124. First and second half-sections 122b, 122c are supported on opposing sides of the longitudinal channel 122a and may include top and/or bottom surfaces that may be arcuate. Distal hook member 124 is disposed on the distal end of the body 122 and includes a first surface 124a, a second surface 124b, and a third surface 124c. First, second, and third surfaces 124a, 124b, and 124c may have any suitable linear and/or curvilinear configuration and may be orientated at any suitable angle relative to the longitudinal axis and/or relative to each other. For example, first surface 124a may be substantially perpendicular to the longitudinal axis, second surface 124b may be substantially parallel to the longitudinal axis, and third surface 124c may be disposed at a substantially acute angle relative to the longitudinal axis.

Release bar 110 includes a drive member 112, a beam engaging hook 114 supported on a distal end of drive member 112, and a handle 116 supported on a proximal end of drive member 112. Drive member 112 is axially movable, e.g., slidably supported, within the longitudinal channel 122a of elongate body member 120 so that beam engaging hook 114 extends from the longitudinal channel 112a at any suitable angle, for example, perpendicularly or substantially perpendicularly. Beam engaging hook 114 includes a trailing surface 114a, a bottom surface 114b, and a leading surface 114c that may have any suitable linear or curvilinear configuration and may be disposed at any suitable angle relative to the longitudinal axis, for example, an acute, perpendicular, or substantially perpendicular angles relative to the longitudinal axis.

Handle 116 may have any suitable shape including ergonomic configurations.

Gripping assembly 130 is supported on the upper surface of body 122 of elongate body member 120. Gripping assembly 130 includes a base 132 that pivotably supports a first panel 134 and a second panel 136 by a pair of pins 138a. As seen in FIG. 7, base 132 defines a pair of channels 132a that extend between proximal and distal ends of base 132. Each channel 132a may be open at the proximal end of base 132 to receive one of pins 138a and closed at the distal end of base 132 to limit axial movement of the respective pin 138a within the respective channel 132a. First panel 134 includes a pivoting segment or spine 134c and a gripping segment 134b. Pivoting segment or spine 134c defines a pin passage 134a therethrough that receives one of pins 138a. Similarly, second panel 136 includes a pivoting segment or spine 136c and a gripping segment 136b. Pivoting segment or spine 136c defines a pin passage 136a therethrough that receives the other pin 138a.

As shown in FIGS. 9-11, an electromechanical, hand-held, powered surgical instrument 10 includes a handle assembly 20, a shaft assembly 30, and an end effector 40 that mechanically and electrically cooperate to manipulate tissue "T." For a detailed description of the construction and operation of exemplary electromechanical, hand-held, powered surgical instrument 10, reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire contents of each of which are hereby incorporated herein by reference.

Notably, end effector 40 is selectively attachable to shaft assembly 30 and includes a first jaw member or cartridge receiving assembly 50, a second jaw member or an anvil supporting assembly 60, a drive beam assembly 70, and a sled 80. Cartridge receiving assembly 50 is configured to receive a cartridge 54 including a plurality of fasteners that are formed by the anvil assembly 60 upon deployment from the cartridge 54 when the sled 80 is distally axially advanced with the drive beam assembly 70 through the cartridge 54. Cartridge receiving assembly 50 defines a channel 52 therethrough. Drive beam assembly 70 includes a beam 72 (e.g., an I-beam, E-beam, etc.) secured to a bar member 74. Beam 72 includes a top portion 72a, bottom portion 72b and a blade 72c supported between the top and bottom portions 72a, 72b. For a detailed description of the construction and operation of end effector 40, reference may be made to U.S. Patent Publication No. 2009/0314821, filed on Aug. 31, 2009, the entire contents of which are hereby incorporated by reference herein.

With reference to FIGS. 12-15, release tool or assembly 100 may be secured to end effector 40 after end effector 40 is detached from surgical stapling apparatus 10. Notably, release tool or assembly 100 is configured to retract drive beam assembly 70 to a proximal position relative to cartridge receiving and anvil supporting assemblies 50, 60 to enable end effector 40 to be repositioned from a closed configuration to an open configuration, as will be described in greater detail below.

Release or tool assembly 100 is used when drive beam assembly 70 has become stuck or jammed during a firing of surgical stapling apparatus 10, and wherein drive beam assembly 70 may not be retracted using the retraction/opening commands/features of surgical stapling apparatus 10. With drive beam assembly 70 so stuck, upon the end effector 40 being detached from surgical stapling apparatus 10, release tool or assembly 100 is secured to end effector 40. Initially, distal hook member 124 of release tool or assembly 100 is inserted into a distal end of channel 52 of cartridge receiving assembly 50, specifically distally of beam 72, so that release tool or assembly 100 is disposed at an acute angle relative to end effector 40. With release bar 110 in an advanced or distal position, relative pivoting movement between release tool or assembly 100 about the distal end of release tool or assembly 100 (i.e., about distal hook member 124) approximates end effector 40 and release tool or assembly 100 so that release tool or assembly 100 is supported on end effector 40 in a parallel or substantially parallel relationship with end effector 40. In this regard, distal hook member 124 secures a distal end of release tool or assembly 100 to end effector 40 so that beam engaging hook 114 is disposed distally of beam 72.

Figure 16:
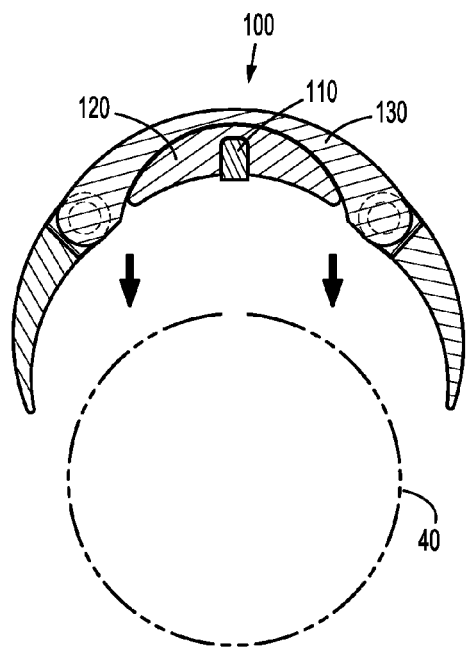
Figure 17:
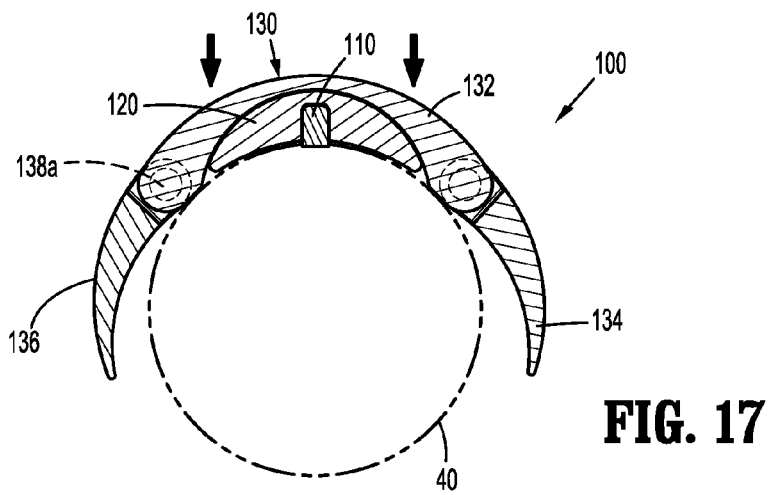
Figure 18:
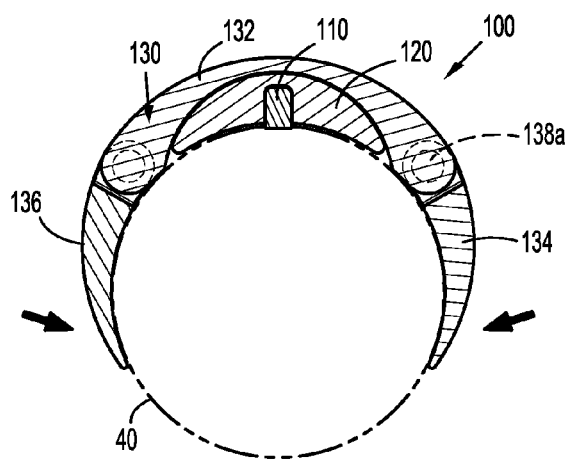

Referring also to FIGS. 16-18, upon or following approximating release tool or assembly 100 and end effector 40, first and second panels 134, 136 are pivoted about pins 138a relative to elongate body member 120. In this regard, first and second panels 134, 136 pivot in opposing directions toward end effector 40 to secure release tool or assembly 100 to end effector 40. Upon being approximated into engagement with end effector 40, first and second panels 134, 136 secure release tool or assembly 100 to end effector 40.

Figure 21:
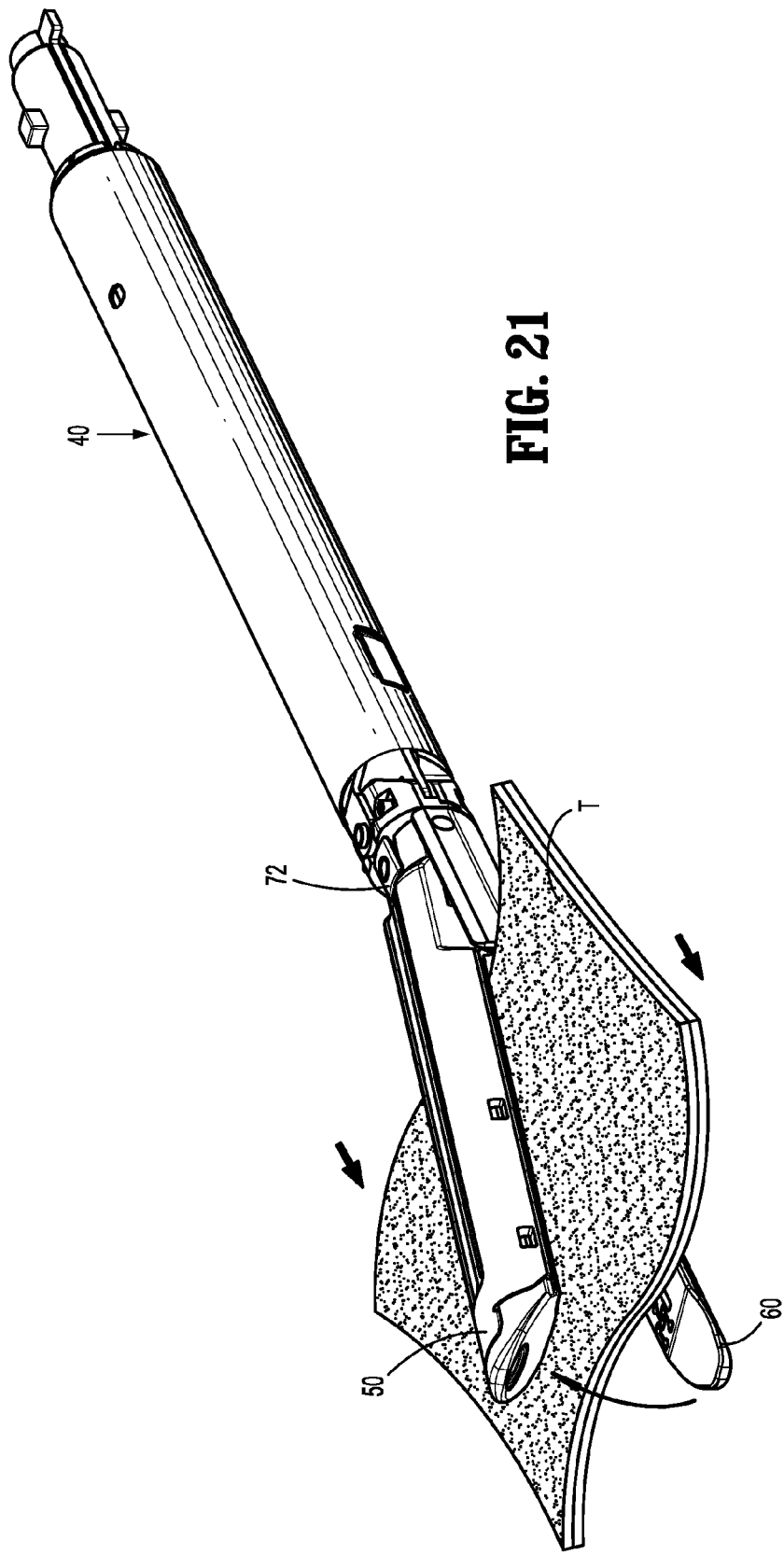
FIG. 21 is a perspective view illustrating the end effector releasing tissue after the drive beam of the end effector has been retracted to the proximal position.

Turning now to FIGS. 19-21, with distal hook member 124 held in position in a distal end of channel 52 of cartridge receiving assembly 50, handle 116 of release bar 110 is then drawn proximally with sufficient force to retract beam engaging hook 124 so that trailing surface 114a of beam engaging hook 124 contacts a leading surface of top portion 72a of beam 72. Further proximal drawing of handle 116 retracts the stuck beam 72 proximally to a proximal position. Release or tool assembly 100 may then be removed by pivoting first and second panels 134, 136 away from end effector 40 and separating release assembly 100 from end effector 40. In this regard, cartridge receiving assembly 50 and anvil supporting assembly 60 may be unapproximated to an open configuration to release any tissue entrapped between cartridge receiving assembly 50 and anvil supporting assembly 60.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. An independent release tool for an end effector of a surgical stapling apparatus, the end effector having a pair of jaw members and a drive beam assembly configured for axial movement through the pair of jaw members, the release tool comprising:
   an elongate body member having distal and proximal ends;
   a gripping assembly secured to the elongate body member and configured to secure the elongate body member to the end effector of the surgical stapling apparatus; and
   a release bar supported by the elongate body member and being axially movable relative to elongate body member, the release bar being configured to engage a beam of the drive beam assembly to retract the beam to a proximal position when the beam is disposed in a position distal of the proximal position.

2. The release tool of claim 1, wherein the distal end of the elongate body member includes a distal hook member.

3. The release tool of claim 1, wherein the release bar includes a beam engaging hook configured to engage the beam upon the proximal movement of the beam engaging hook so that the beam engaging hook retracts the beam to the proximal position.

4. The release tool of claim 3, wherein the release bar includes a drive member secured to the beam engaging hook, the drive member being axially movable to axially move the beam engaging hook.

5. The release tool of claim 4, wherein the release bar includes a handle, the handle being supported on a proximal end of the drive member, the beam engaging hook being supported on a distal end of the drive member.

6. The release tool of claim 1, wherein the gripping assembly includes a panel that pivots relative to the elongate body member.

7. The release tool of claim 6, wherein the gripping assembly includes a first panel and a second panel that pivot in opposing directions relative to the elongate body member.

8. A release tool and end effector kit, the kit comprising:
   an end effector including a pair of jaw members and a beam supported on a drive assembly configured for axial movement through the pair of jaw members, the end effector selectively attachable to a surgical stapling apparatus configured to move the pair of jaw members between open and closed configurations; and a release tool separate from the end effector and the surgical stapling apparatus, the release tool selectively attachable to the end effector, the release tool including:
- an elongate body member;
- a gripping assembly secured to the elongate body member to secure the elongate body member to the end effector; and
- a release bar including a beam engaging hook supported by the elongate body member and being axially movable relative to the end effector when the elongate body member is secured to the end effector, the beam engaging hook of the release bar being engageable with the beam to retract the beam and drive beam assembly to a proximal position when the beam is disposed in a position distal of the proximal position.

9. The release tool and end effector kit of claim 8, wherein the pair of jaw members moves from a closed configuration to an open configuration when the beam engaging hook retracts the beam to the proximal position.

10. The release tool and end effector kit of claim 8, wherein the distal end of the elongate body member includes a hook member.

11. The release tool and end effector kit of claim 8, wherein the gripping assembly includes a panel that pivots relative to the elongate body member.

12. The release tool and end effector kit of claim 8, wherein the beam engaging hook is axially movable relative to the elongate body member.

13. The release tool and end effector kit of claim 8, wherein the pair of jaw members includes an anvil member and a cartridge member, the cartridge member being configured to receive a cartridge that retains a plurality of fasteners.

14. A surgical stapling kit, comprising:
a surgical stapling apparatus including an end effector, the end effector including an anvil supporting member, a cartridge receiving member, and a beam supported on a drive beam assembly that moves axially through the anvil supporting member and the cartridge receiving member; and a release tool independent of the surgical stapling apparatus and the end effector, the release tool selectively attachable to the end effector, the release tool including:
- an elongate body member;
- a pair of panels secured to the elongate body member to secure the release tool to the end effector; and
- a release bar including a beam engaging member, the release bar being supported by the elongate body member and being axially movable relative to the end effector when the release tool is secured to the end effector, the beam engaging member of the release bar being engageable with the beam to retract the beam and the drive beam assembly to a proximal position when the beam is disposed in a position distal of the proximal position.

15. The surgical stapling kit of claim 14, wherein the anvil supporting member and the cartridge receiving member of the end effector move from a closed configuration to an open configuration when the beam engaging member of the release tool retracts the beam and the drive beam assembly to the proximal position.

16. The surgical stapling kit of claim 14, wherein the elongate body member of the release tool includes a distal hook member.

17. The surgical stapling kit of claim 16, wherein the cartridge receiving member of the end effector defines a channel through a top surface thereof, wherein a top portion of the beam axially translates through the channel upon the axial movement of the beam, the distal hook member of the elongate body member being positionable within the channel.

18. The surgical stapling kit of claim 17, wherein a proximal surface of the beam engaging member of the release bar contacts a distal surface of the top portion of the beam when the beam engaging member and the beam are engaged.

19. The surgical stapling kit of claim 14, wherein the panels pivot relative to the elongate body member to secure the release tool to the end effector.

20. The surgical stapling kit of claim 14, wherein the beam engaging member of the release bar is axially movable relative to the elongate body member.

* * * * *